United States Patent [19]
Huber

[11] Patent Number: 5,922,892
[45] Date of Patent: Jul. 13, 1999

[54] PROCESS TO PRODUCE MIDAZOLAM

[75] Inventor: Joel Edward Huber, Mattawan, Mich.

[73] Assignee: Pharmacia & Upjohn Company, Kalamazoo, Mich.

[21] Appl. No.: 09/062,929

[22] Filed: Apr. 20, 1998

Related U.S. Application Data

[62] Division of application No. 08/864,043, May 28, 1997., Pat. No. 5,831,089
[60] Provisional application No. 60/020,677, Jul. 1, 1996.

[51] Int. Cl.$^6$ .................... C07D 211/14; C07D 207/06
[52] U.S. Cl. .............................. 556/137; 540/562
[58] Field of Search ............... 556/137; 540/562

[56] References Cited

U.S. PATENT DOCUMENTS

| | | | |
|---|---|---|---|
| 3,932,325 | 1/1976 | Nakanishi et al. | 544/283 |
| 4,280,957 | 7/1981 | Walser et al. | 540/562 |
| 4,377,523 | 3/1983 | Walser et al. | 540/562 |

OTHER PUBLICATIONS

*J. Heterocyclic Chem.*, 13, pp. 433–437 (1976).
*J. Org. Chem.*, 43, pp. 936–944 (1978).
*Aldrichimica Acta*, 23(1), pp. 13–19 (1990).
*Tetrahedron Letters*, 35(35), pp. 6567–6570 (1994).
*J. Org. Chem.*, 40(2), 153 (1975).

*Primary Examiner*—Richard L. Raymond
*Attorney, Agent, or Firm*—Bruce Stein

[57] ABSTRACT

The present invention discloses new processes in the preparation of midazolam (VII),

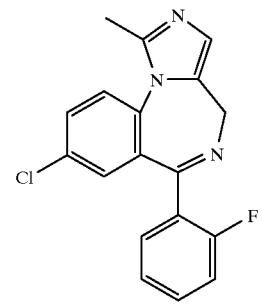

a commercially important pharmaceutical, as well a new intermediates in those processes from a known benzophenone (I) starting material.

6 Claims, No Drawings

PROCESS TO PRODUCE MIDAZOLAM

CROSS-REFERENCE TO RELATED APPLICATIONS

The present patent application is a divisional of U.S. patent application Ser. No. 08/864,043, filed May 28, 1997, now U.S. Pat. No. 5,831,089, which claims the benefit of U.S. provisional application Ser. No. 60/020,677 filed Jul. 1, 1996, under 35 USC §119(e)(i).

BACKGROUND OF THE INVENTION

1. Field of the Invention

The present invention includes two processes which are useful in the production of midazolam.

2. Description of the Related Art

U.S. Pat. Nos. 4,280,957 and 4,377,523 disclose midazolam (VII) and processes for its production.

*J. Heterocyclic Chem.*, 13, 433 (1976) discloses the conversion of the amino benzophenone starting material (I) to the corresponding nitro-nitrone (IV). The amino benzophenone (I) was transformed to the corresponding dihydroquinazoline which is then reacted with manganese dioxide to form the quinazoline (III). The quinazoline (III) is then transformed to the corresponding nitroolefin (IV) by reaction with lithium amide and nitromethane in dimethylsulfoxide.

*J. Org. Chem.*, 43, 936 (1978) discloses the conversion of the nitroolefin (IV) to midazolam (VII). The nitroolefin (IV) is reduced to the amine (V) by catalytic hydrogenation. The amine (V) is transformed to the corresponding benzodiazepine (VI) by known methods. The benzodiazepine (VI) is then oxidized to midazolam (VII) in about 58% yield by use of manganese dioxide.

*Aldrichimica Acta*, 23(1), 13–19 (1990) discloses various reactions where "TPAP" is used as the catalyst for oxidation of alcohols. Example 41 discloses the oxidation of a 1-hydroxy-3-benzyloxycyclohexane derivative to the corresponding α;β-unsaturated cyclohexanone. *Tetrahedron Letters*, 35(35), 6567–6570 (1994) discloses oxidation of indoline to produce indole by use of TPAP. The use of TPAP in the present invention is in a more complex ring system and it is advantageous to pretreat the TPAP with an alcohol before usage.

*J. Org. Chem.*, 40(2), 153 (1975) discloses compound 10 which is similar to the midazolam-nitrone (IX) of the present invention but it does not have a fluorine atom required for pharmacological activity.

SUMMARY OF INVENTION

Disclosed is an alkoxy compound of the formula (II)

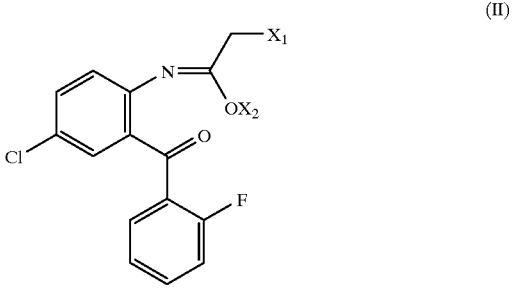

where $X_1$ is —Cl or —Br, and where $X_2$ is $C_1$–$C_4$ alkyl or —$CH_2$—φ.

Also disclosed is a process for the production of the alkoxy compound of formula (II) where $X_1$ is —Cl or —Br; where $X_2$ is $C_1$–$C_4$ alkyl or —$CH_2$—φ; which comprises:

(1) contacting 2-amino-5-chloro-2'-fluorobenzophenone (I) with an orthoester of the formula (XI)

$$X_1\text{—}CH_2\text{—}C(OX_2)_3 \qquad (XI)$$

where $X_1$ and $X_2$ are as defined above, (2) heating the reaction mixture to a temperature of about 40 to about 90° in the presence of an acid catalyst.

Further disclosed is a process for the production of a quinazoline compound of formula (III) where $X_1$ is —Cl or —Br which comprises:

(1) contacting 2-amino-5-chloro-2'-fluorobenzophenone (I) with an orthoester of formula (XI)

$$X_1\text{—}CH_2\text{—}C(OX_2)_3 \qquad (XI)$$

where $X_2$ is $C_1$–$C_4$ alkyl or —$CH_2$—φ and where $X_1$ is as defined above, (2) heating the reaction mixture to a temperature of about 40° to about 90° in the presence of an acid catalyst, (3) cooling the reaction mixture of step (2) to about +10° to about −20°, (4) contacting the cooled reaction mixture of step (3) with hydroxylamine and a base.

Additionally disclosed is a process for the production of midazolam (VII) which comprises contacting 8-chloro-3,4-dihydro-6-(2-fluorophenyl)-1-methyl-4H-imidazo[1,5-a]benzodiazepine (VI) with TPAP.

Also disclosed are the useful intermediates in the production of midazolam which are:

7-chloro-5-(2-fluorophenyl)-2,3-dihydro- 1H-1,4-benzodiazepine-2-methanamine-4-oxide (VIII), 8-chloro-6-(2-fluorophenyl)-3a,4-dihydro- 1-methyl-3H-imidazo[1,5-a][1,4]benzodiazepine-5-oxide (IX) and 8-chloro-6-(2-fluorophenyl)-1-methyl-4H-imidazo[1,5-a][1,4]benzodiazepine-5-oxide (X).

Further disclosed is a process for producing TPAP in an activated form which comprises contacting unactivated TPAP with an alcohol.

DETAILED DESCRIPTION OF THE INVENTION

Midazolam (VII), 8-chloro-6-(2-fluorophenyl)- 1-methyl-4H-imidazo[1,5-a]benzodiazepine, is known, see U.S. Pat.

Nos. 4,280,957 and 4,377,523. These patents disclose methods to make midazolam. *J. Heterocyclic Chem.*, 13, 433 (1976) and *J. Org. Chem.*, 43, 936 (1978) also discloses a process to produce midazolam (VII).

One process of the present invention transforms the starting material benzophenone (I) to the corresponding alkoxy compound (II). Another process transforms the benzophenone (I) to the corresponding quinazoline (III) by an improved process. Another process is an improved method of oxidizing 8-chloro-3,4-dihydro-6-(2-fluorophenyl)-1-methyl-4H-imidazo[1,5-a]benzodiazepine (VI) to midazolam (VII). Still another process is a method to activate the TPAP reagent.

The first process involves the contacting the benzophenone (I), 2-amino-5-chloro-2'-fluorobenzophenone, with the orthoester (XI), $X_1$—$CH_2$—$C(OX_2)_3$, where $X_1$ is —Cl or —Br, $X_2$ is $C_1$–$C_4$ alkyl or —$CH_2\phi$ and heating the reaction mixture to a temperature of about 40 to about 90° in the presence of an acid catalyst. Suitable acids include any acid with a $pK_a$ of 0.5 to 4.8; preferred are acetic acid, chloroacetic acid, dichloroacetic, trichloroacetic, fluoroacetic, difluoroacetic, trifluroacetic acid and p-TSA; most preferred is acetic acid. It is preferred that $X_1$ is —Cl and that $X_2$ is $C_1$ alkyl. It is preferred the reaction mixture be heated to from about 55 to about 65°. It is preferred that the process be performed under reduced pressure. The reduced pressure is not required but it preferred to remove the alcohol (methanol) which is produced from —$OX_2$ (when $X_2$ is $C_1$ alkyl) and therefore help drive the reaction to completion. The reaction of the 2-amino-5-chloro-2'-fluorobenzophenone (I) with the orthoester (XI) produces the alkoxy compound (II). The alkoxy compound (II) can be isolated if desired (by methods known to those skilled in the art) if desired. However, it is preferred not to isolate the alkoxy compound (II) but to react it in situ without isolation to produce the corresponding quinazoline (III).

The alkoxy compound (II) is dissolved in a suitable solvent such as an alcohol, preferably $C_1$–$C_4$ alcohols and cooled to about −10 to about 20°, preferably about 0°. This mixture is then reacted with hydroxylamine, either as the free base, salt or aqueous formulation. The commercially available 40% hydroxylamine is operable. If the salt is used the reaction is performed in the presence of a base. Suitable bases are those which will transform hydroxylamine in the salt form to hydroxylamine free base. These bases include bicarbonate, carbonate, hydroxide and salts of organic acids such as sodium acetate. The reaction mixture is acidified to a pH of about 5 with an acid such as acetic acid and stirred at about −10 to about 25°. The desired quinazoline (III) is isolated by means known to those skilled in the art. This material can be use further in the process of CHART A without additional purification.

Another process of the invention is the oxidation of 8-chloro-3,4-dihydro-6-(2-fluorophenyl)-1-methyl-4H-imidazo[1,5-a]benzodiazepine (VI) to midazolam (VII). It is preferred that 8-chloro-3,4-dihydro-6-(2-fluorophenyl)-1-methyl-4H-imidazo[1,5-a]benzodiazepine (VI) be in the free base form. If it is not, the salt form should be reacted with a suitable base to produce the free base of 8-chloro-3,4-dihydro-6-(2-fluorophenyl)-1-methyl-4H-imidazo[1,5-a]benzodiazepine (VI). The oxidative process of the present invention of transforming 8-chloro-3,4-dihydro-6-(2-fluorophenyl)-1-methyl-4H-imidazo[1,5-a]benzodiazepine (VI) to midazolam (VII) uses a catalyst known as "TPAP" which is tetra-n-propylammonium perruthenate. The catalyst is prepared by contacting it with powdered sieves and a secondary alcohol in an appropriate solvent at a temperature of about 10 to about 60°. It is preferred that the powdered sieves be from three to about ten angstroms, preferably about 4 angstroms. Most all secondary alcohols without other functional groups that are liquids at 20–25° are operable, preferred are i-propanol, cyclohexanol and i-butanol; more preferred is i-propanol. Most common non-reactive organic solvents are operable, preferred are acetonitrile and methylene chloride, more preferred is acetonitrile. Depending on reaction conditions, the preparation of the catalyst takes from a few minutes to days or weeks.

The oxidation process of transforming 8-chloro-3,4-dihydro-6-(2-fluorophenyl)-1-methyl-4H-imidazo[1,5-a]benzodiazepine (VI) to midazolam (VII) is performed by contacting 8-chloro-3,4-dihydro-6-(2-fluorophenyl)-1-methyl-4H-imidazo[1,5-a]benzodiazepine (VI) with the TPAP catalyst. It is preferred that the contacting be performed in the presence of molecular sieves. It is preferred that the molecular sieves be from three to about ten angstroms, preferably about 4 angstroms. It is preferred that the contacting be performed in the temperature range of about 10 to about 80°, more preferably from about 30 to about 40°. Suitable solvents for the process include acetonitrile, methylene chloride, toluene and dimethylformamide and mixtures thereof.

CHART B discloses an alternate series of steps to transform the nitroolefin (IV) to midazolam. The nitroolefin (IV) is known, see *J. Heterocyclic Chem.*, 13, 433 (1976). This process does not remove the "N-oxide" or "nitrone" group at this point but carries it along and it is removed in the final step producing midazolam (VII), see EXAMPLEs 6–9.

Also disclosed is a process to make the "TPAP" catalyst operable. It was found that if used as purchased it was not operable. To activate the catalyst and make it useful it must be reacted with an alcohol, preferably a secondary alcohol, more preferably i-propyl alcohol. It is preferable to add molecular sieves of about three to about 10 angstrons, preferably about 4 angstroms and heat the TPAP and alcohol to about 25 to about 50° with stirring for a about two to about 24 hours. It is preferred to use about 22 to about 66 mL of alcohol for every 100 g of TPAP.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$—$C(=Z_1)H$. Groups $R_i$ and $R_j$ would represent monovalent variable substituents if attached to the formula $CH_3$—$CH_2$—$C(R_i)(R_j)$—H. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom.

Chemical formulas or portions thereof drawn in a linear fashion represent atoms in a linear chain. The symbol "-" in general represents a bond between two atoms in the chain. Thus $CH_3$—O—$CH_2$—CH($R_i$)—$CH_3$ represents a 2-substituted-1-methoxypropane compound. In a similar fashion, the symbol "=" represents a double bond, e.g., $CH_2$=C($R_i$)—O—$CH_3$, and the symbol "≡" represents a triple bond, e.g., HC≡C—CH($R_i$)—$CH_2$—$CH_3$. Carbonyl groups are represented in either one of two ways: —CO— or —C(=O)—, with the former being preferred for simplicity.

The carbon atom content of variable substituents is indicated in one of two ways. The first method uses a prefix to the entire name of the variable such as "$C_1$–$C_4$", where both "1" and "4" are integers representing the minimum and maximum number of carbon atoms in the variable. The prefix is separated from the variable by a space. For example, "$C_1$–$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$–$C_4$ alkoxycarbonyl describes a group $CH_3$—$(CH_2)_n$—O—CO— where n is zero, one or two. By the second method the carbon atom content of only each portion of the definition is indicated separately by enclosing the "$C_i$–$C_j$" designation in parentheses and placing it immediately (no intervening space) before the portion of the definition being defined. By this optional convention ($C_1$–$C_3$)alkoxycarbonyl has the same meaning as $C_2$–$C_4$ alkoxy-carbonyl because the "$C_1$–$C_3$" refers only to the carbon atom content of the alkoxy group. Similarly while both $C_2$–$C_6$ alkoxyalkyl and ($C_1$–$C_3$)alkoxy($C_1$–$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

II. DEFINITIONS

Midazolam refers to 8-chloro-6-(2-fluorophenyl)-1-methyl-4H-imidazo[1,5-a]benzodiazepine.

All temperatures are in degrees Centigrade.

TLC refers to thin-layer chromatography.

TPAP refers to tetra-n-propylammonium perruthenate.

HPLC refers to high pressure liquid chromatography.

THF refers to tetrahydrofuran.

DMSO refers to dimethylsulfoxide.

DMF refers to dimethylformamide.

DDQ refers to 2,3-dichloro-5,6-dicyano-1,4-benzoquinone.

DMAC refers to dimethylacetamide.

LDA refers to lithium diisopropylamide.

p-TSA refers to p-toluenesulfonic acid monohydrate.

TEA refers to triethylamine.

Magnesol refers to a commercial magnesium silicate adsorbant.

Solka floc refers to a commercial adsobant.

Chromatography (column and flash chromatography) refers to purification/separation of compounds expressed as (support, eluent). It is understood that the appropriate fractions are pooled and concentrated to give the desired compound(s).

IR refers to infrared spectroscopy.

UV refers to ultraviolet spectroscopy.

PMR refers to proton magnetic resonance spectroscopy, chemical shifts are reported in ppm (δ) downfield from TMS.

CMR refers to C-13 magnetic resonance spectroscopy, chemical shifts are reported in ppm (δ) downfield from TMS.

NMR refers to nuclear (proton) magnetic resonance spectroscopy, chemical shifts are reported in ppm (δ) downfield from tetramethylsilane.

TMS refers to trimethylsilyl.

–φ refers to phenyl ($C_6H_5$).

MS refers to mass spectrometry expressed as m/e, m/z or mass/charge unit. [M+H]$^+$ refers to the positive ion of a parent plus a hydrogen atom. EI refers to electron impact. CI refers to chemical ionization. FAB refers to fast atom bombardment.

When solvent pairs are used, the ratios of solvents used are volume/volume (v/v).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

Tetra-n-propylammonium perruthenate (TPAP)

Tetra-n-propylammonium perruthenate (100 mg) and 4 Å powdered sieves (200 mg) in acetonitrile (2.0 mL) and i-propanol (65 μL, 3.0 eq) is added. A slight exotherm to about 35° is noted and the mixture is stirred at 20–25° for 4.5 hr and then is used as is.

EXAMPLE 2

Methyl-1-chloromethyl-2'-amino-5'-chloro-2"-fluorobenzophenone imidate (II)

Trimethyl-α-chloro-orthoacetate (XI, 3.49 mL) followed by acetic acid (100 μl) is added to 2-amino-5-chloro-2'-fluorobenzophenone (I, 3.47 g). The mixture is heated to about 60° with stirring for 1 hr during which a controlled vacuum (~600 nm of vac.) is applied to remove the methanol being generated and give the title compound, TLC (silica gel; ethyl acetate/hexane, 20/80) $R_f$=0.46.

EXAMPLE 3

2-Chloromethyl-4-(2-fluorophenyl)-6-chloro-1,2-dihydroquinazoline-3-oxide (III)

Methyl-1-chloromethyl-2'-amino-5'-chloro-2"-fluorobenzophenone imidate (II, EXAMPLE 2) is dissolved in i-propanol (8 mL) and the resulting mixture is cooled to –5°. To this mixture is added, in one portion, a slurry of hydroxylamine hydrochloride (1.93 g) and sodium acetate (2.85 g) in water (7.8 mL). Acetic acid (3.5 mL) is added and the slurry is stirred for 18 hr at –5 to 16°. The crude product is precipitated by the addition of water (10 mL). The mixture is stirred at 23° for 1 hr and the solids are collected by (vacuum) filtration, washed with water/i-propanol (80/20, 10 mL) followed by i-propanol (7 mL) to give the title compound, TLC (silica gel; ethyl acetate/hexane, 20/80) $R_f$=0.15.

EXAMPLE 4

8-Chloro-3,4-dihydro-6-(2-fluorophenyl)-1-methyl-4H-imidazo[1,5-a]benzodiazepine (VI)

A mixture of 8-chloro-3,4-dihydro-6-(2-fluorophenyl)-1-methyl-4H-imidazo[1,5-a]benzodiazepine methanesulfonate (VI, 100 g), ammonium hydroxide (10%, 500 mL) and methylene chloride (500 mL) are mixed for 10 min at 20–25°. The methylene chloride layer is separated and the aqueous layer is extracted with methylene chloride (250 mL and 2×100 mL). The combined organic layers are dried with anhydrous magnesium sulfate, filtered and concentrated under reduced pressure give the title compound.

EXAMPLE 5

Midazolam (VII)

A solution of trimethylamine oxide (1.111 g) in acetonitrile (30 mL) is heated to 35° and after 15 min. of equilibration, 5 mL of solvent is distilled off under reduced pressure. Then 4 Å powdered sieves (PREPARATION 1, 2.50 g) and 8-chloro- 3,4-dihydro-6-(2-fluorophenyl)-1-methyl-4H-imidazo[1,5-a]benzodiazepine (VI, EXAMPLE 4, 1.639 g) is added using acetonitrile (about 5 mL) for a rinse. The above catalyst slurry from EXAMPLE 1 is added using acetonitrile (1 mL) for a rinse. This slurry is stirred under 200–300 mm of vacuum at 36–42° for a total of 70 hr. The reaction is followed by HPLC on a 25 cm Prodigy ODS-2 column. After 69 hr, ethyl acetate (40 mL) is added and the warm reaction mixture was filtered through a 24 mm high×44 mm wide magnesol bed that is prepared in ethyl acetate. The first five-40 mL fractions of ethyl acetate are collected by gravity feed and since, TLC indicated they contained most of the midazolam, they are combined and concentrated under reduced pressure with a little heat. The concentrate is taken up in warm ethyl acetate (3.0 mL) and midazolam began to crystallize. Heptane (10 mL) is added in portions to increase the recovery. This slurry is remains at 20–25° overnight and then, after standing 1 hr at −10°, the solids were collected, washed with heptane/ethyl acetate (3/1, 2×1.7 mL) and dried at 50° for 2 hr to give the title compound.

EXAMPLE 6

7-Chloro-5-(2-fluorophenyl)-2,3-dihydro-1H-1,4-benzodiazepine-2-methanamine-4-oxide (VIII)

To 7-chloro-1,3-dihydro-5-(2-fluorophenyl)-2-nitromethylene-2H-1,4-benzodiazepine (IV, *J. Heterocyclic Chem.*, 13, 433 (1976)—compound 4b, 40 g, 115 mmol) and sodium borohydride (6.68 g, 176 mmol, 10 mesh) is added THF (100 ml) and i-propyl alcohol (50 ml). The resulting slurry is treated with a slow addition of water (3.1 ml, 176 mmol) while the temperature is maintained at about 23°. The reaction mixture is stirred for 2 hr. Water (9.3 ml) is added slowly to quench the reaction mixture. Methanol (50 ml) is used to facilitate transfer of the reaction mixture to a 500 ml capacity stainless steel Buchi hydrogenator. Raney nickel (40 g of water wet material) is added and the hydrogenation is performed at 5° and 60 psig pressure. After 17 hr, HPLC showed the reduction is complete. The reaction mixture is removed from the Buchi and the hydrogenator is rinsed with methanol (200 ml). The combined reaction mixture and rinses are filtered through a 5 g pad of solka floc to remove spent catalyst. The catalyst cake is then rinsed with methanol (200 ml). The combined filtrate and rinses are concentrated. Water is added to the concentrate. The product is extracted from the aqueous layer using ethyl acetate (200 ml). The ethyl acetate extract is concentrated to near dryness to azeotrope any residual water. Finally, ethyl acetate (600 ml) is used to dissolve the crude product and the mixture is heated to 50–60°. Then oxalic acid (10.36 g, 115 mmol) is added. The slurry that forms is stirred overnight at 20–25° and is then cooled to 0° for rand the product is collected by vacuum filtration. The product is washed with ethyl acetate (100 ml) and dried at 40° in a vacuum oven to give the title compound as the oxalic salt, mp=144–148°; TLC (methylene chloride/methanol/ammonium hydroxide, 90/10/1) $R_f$=0.17.

EXAMPLE 7

8-Chloro-6-(2-fluorophenyl)-3a,4-dihydro-1-methyl-3H-imidazo[1,5-a][1,4]benzodiazepine-5-oxide (IX)

A slurry of 7-chloro-5-(2-fluorophenyl)-2,3-dihydro-1H-1,4-benzodiazepine-2-methanamine-4-oxide oxalate salt (VIII, EXAMPLE 6, 35 g, 85 mmol) and triethylorthoacetate (23.5 ml, 128 mmol) in acetonitrile (175 ml) is stirred at reflux for 2 hr during which time the 7-chloro-5-(2-fluorophenyl)-2,3-dihydro-1H-1,4-benzodiazepine-2-methanamine-4-oxide (VIII) dissolves and ethanol/acetonitrile (about 75 ml) is removed by distillation under ordinary pressure. TLC and HPLC analysis shows the reaction is complete. The temperature is adjusted to 40° and methyl t-butyl ether (175 ml) is added dropwise over about 1 hr. The resulting slurry is cooled to 5°, stirred 1 hr, the solids are collected and are washed with t-butyl ether. The product is dried in the vacuum oven at 35° to give the title compound as the oxalate salt, mp=178–180°; TLC (methylene chloride/methanol/ammonium hydroxide, 90/10/1) $R_f$=0.28.

EXAMPLE 8

8-Chloro-6-(2-fluorophenyl)-1-methyl-4H-imidazo[1,5-a][1,4]benzodiazepine-5-oxide (X)

The active TPAP is prepared by slurring three commercial TPAP samples (323 mg) in acetonitrile (3 ml) and treating each sample with i-propyl alcohol (211 μL).

8-Chloro-6-(2-fluorophenyl)-3a,4-dihydro-1-methyl-3H-imidazo[1,5-a][1,4]benzodiazepine-5-oxide (IX, EXAMPLE 7, 20.00 g, 46 mmol) is partitioned between ammonium hydroxide (10%, 100 ml) and methylene chloride (100 ml). The layers are separated and the aqueous phase is extracted with additional methylene chloride (2×50 ml). The combined organic extracts are concentrated to dryness and the solids are redissolved in acetonitrile (200 ml). To this mixture is added powdered molecular sieves (20 g) and trimethylamine-N-oxide (7.6g, 68 mmol) followed by one activated TPAP sample from above. The reaction mixture is heated to reflux and the next sample of TPAP and an additional trimethylamine-N-oxide (7.66 g, 68 mmol) is added after 6 hr and again after 18 hr. The mixture is heated at reflux for 42 hr at which time HPLC shows only 6% starting material remaining. The reaction mixture is concentrated to dryness and ethyl acetate (100 ml) is added back. The slurry is chromatographed (magnesol, 100 g) until no more product is eluding with et acetate. The combined column fractions are concentrated to about 60 ml and heptane (140 ml) is added slowly. The product is cooled to −15° overnight, collected by vacuum filtration, washed with cold heptane and dried in the vacuum oven at 40° to give the title compound.

EXAMPLE 9

Midazolam (VII)

To a mixture of 8-chloro-6-(2-fluorophenyl)-1-methyl-4H-imidazo[1,5-a][1,4]benzodiazepine-5-oxide (X, EXAMPLE 8, 3.42 g, 10 mmol) and sodium hypophosphite (5.3 g, 50 mmol) in i-propyl alcohol (34 ml) and water (34 ml) is added 5% palladium on carbon (342 mg, 53% water wet). The slurry is stirred at 23° for 2 hr. TLC and HPLC analysis shows the reaction is complete. The reaction mixture is filtered through a small bed of solka floc and concentrated to near dryness. The concentrate is partitioned between water (50 ml) and ethyl acetate (50 ml). The ethyl acetate layer is collected and the aqueous layer extracted with ethyl acetate (50 ml). The combined ethyl acetate extracts are concentrated and then redissolved in hot i-isopropyl alcohol (12 ml). The mixture is cooled gradually to 20–25°, seeded and cooled to −15° overnight. The solids are collected, washed with cold i-propyl alcohol and dried in the vacuum oven to give the title compound, TLC (methylene chloride/methanol/ammonium hydroxide, 90/10/1) $R_f$=0.59; HPLC (methanol/0.05M ammonium hydroxide/acetonitrile, 55/35/10) $R_t$=9.5 min.

EXAMPLE 10
7-Chloro-5-(2-fluorophenyl)-2,3-dihydro-1H-1,4-benzodiazepine-2-methanamine-4-oxide (VIII)

Following the general procedure of EXAMPLE 6 and making non-critical variations (using 150 and 90 psig), the title compound is obtained, NMR (300 MHz, DMSO) 2.62, 3.83, 4.15, 6.48, 6.60, 6.95, 7.10, 7.26, 7.45 and 8.29 δ; CMR (DMSO) 160.4, 158.5, 144.9, 137.3, 131.6, 130.6, 129.2, 128.9, 124.4, 123.1, 122.9, 120.6, 119.9, 117.8, 115.9, 115.7, 64.4, 54.5 and 45.8 δ.

EXAMPLE 11
8-Chloro-6-(2-fluorophenyl)-3a,4-dihydro-1-methyl-3H-imidazo[1,5-a][1,4]benzodiazepine-5-oxide (IX)

Following the general procedure of EXAMPLE 7 and making non-critical variations (trimethylorthoacetate in place of triethylorthoacetate), the title compound is obtained, NMR (300 MHz, CDCl$_3$) 1.78, 2.68, 3.95, 4.21, 4.60, 4.76, 6.99, 7.43 and 7.59 δ; CMR (CDCl$_3$) 178.4, 161.7, 161.2, 158.4, 138.1, 137.8, 134.4, 132.1, 131.9, 131.4, 130.1, 124.3, 120.8, 120.6, 116.7, 116.4, 69.3, 66.0, 57.5, 29.7 and 14.6 δ.

EXAMPLE 12
8-Chloro-6-(2-fluorophenyl)-1-methyl-4H-imidazo[1,5-a][1,4]benzodiazepine-5-oxide (X)

Following the general procedure of EXAMPLE 8 and making non-critical variations, the title compound is obtained, mp=224–226°; TLC (methylene chloride/methanol/ammonium hydroxide, 90/10/1) R$_f$=0.49; NMR (300 MHz, CDCl$_3$) 7.3, 5.04 and 2.59 δ; CMR (CDCl$_3$) 161.75, 158.4, 144.5, 134.9, 133.4, 132.2, 132.0, 131.9, 131.5, 130.5, 130.3, 129.9, 1290.6, 126.0, 124.2, 124.1, 121.1, 121.0, 116.5, 116.2, 64.1, 59.9, 25.3 and 14.9 δ.

CHART A

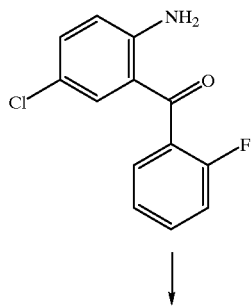

(I)

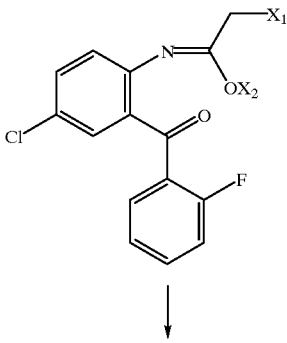

(II)

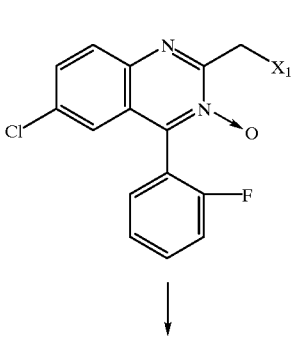

(III)

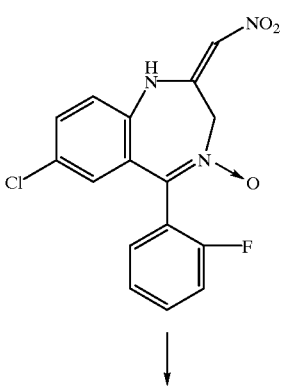

(IV)

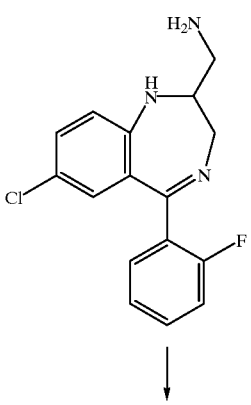

(V)

11
-continued

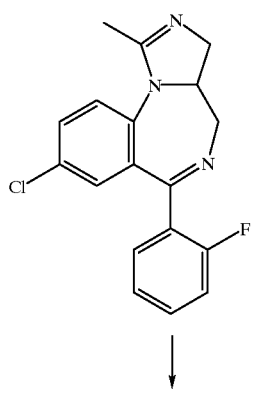

(VI)

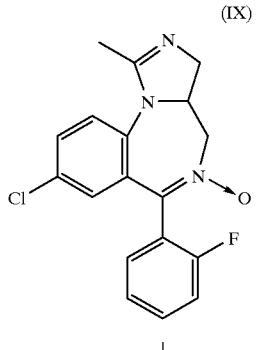

(IX)

(VII)

CHART B

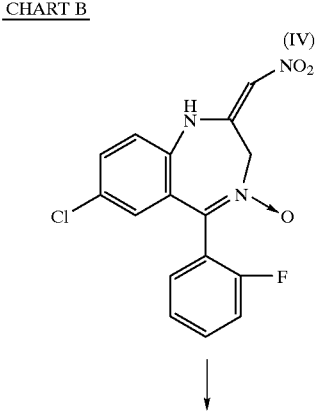

(IV)

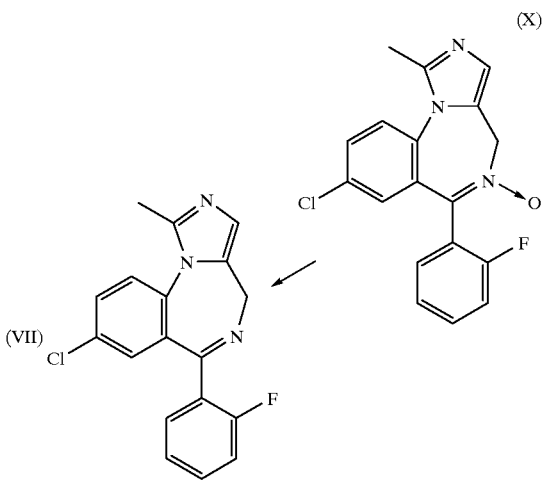

(X)

(VIII)

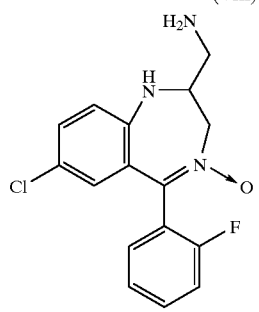

I claim:

1. A process for producing TPAP in an activated form which comprises contacting unactivated TPAP with an alcohol.

2. A process for producing TPAP according to claim 1 where the alcohol is a secondary alcohol.

3. A process for producing TPAP according to claim 1 where the alcohol is i-propyl alcohol.

4. A process for producing TPAP according to claim 1 where the process is heated from about 25 to about 50°.

5. A process for producing TPAP according to claim 1 where the process is performed in the presence of molecular sieves.

6. A process for producing TPAP according to claim 5 where the molecular sieves are from about 3 to about 10 angstroms.

* * * * *